US00PP13172P2

(12) United States Plant Patent
Zary

(10) Patent No.: US PP13,172 P2
(45) Date of Patent: Nov. 5, 2002

(54) MINIATURE ROSE PLANT NAMED 'JACLAMAR'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/756,980

(22) Filed: Jan. 9, 2001

(65) Prior Publication Data

US 2002/0092048 P1 Jul. 11, 2002

(51) Int. Cl.[7] ..... A01H 5/00

(52) U.S. Cl. ..... Plt./118

(58) Field of Search ..... Plt./118, 116

*Primary Examiner*—Bruce R. Campell
*Assistant Examiner*—June Hwu
(74) *Attorney, Agent, or Firm*—Klarquist Sparkman, LLP

(57) ABSTRACT

Minature rose plant having a deep yellow flower color; long shelf life; ease of propagation as an own-root cutting; and an ability to force well throughout the year.

1 Drawing Sheet

BOTANICAL CLASSIFICATION

*Rosa hybrida.*

VARIETY DENOMINATION

'JAClamar'.

BACKGROUND OF THE INVENTION

The present invention relates to a new and distinct variety of rose plant of the miniature class which was originated by me by crossing the variety MORpoly, U.S. Plant Pat. No. 8,453 with an unnamed variety.

BRIEF SUMMARY OF THE INVENTION

The primary objective of this breeding was to produce a new rose variety having a compact plant habit, dense foliage and well-formed flowers of the female parent, combined with the deep yellow flower color, heavy petal substance and long shelf life of the male parent. The objective was substantially achieved, along with other desirable improvements, as evidenced by the following unique combination of characteristics that are outstanding in the new variety and that distinguish it from its parents, as well as from all other varieties of which I am aware:

1. Deep yellow flower color;
2. Long shelf life (i.e., plant will remain in bloom about fifteen to eighteen days);
3. Ease of propagation as an own-root cutting; and
4. Ability to force well throughout the year.

Asexual reproduction of this new variety by cuttings, as performed at Somis, Calif., shows that the foregoing and all other characteristics and distinctions come true to form and are established and transmitted through succeeding propagations. Plants can be grown in pots from cuttings to bloom in about fourteen weeks.

BRIEF DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated.

Parentage:
*Seed parent.*—MORply (U.S. Plant Pat. No. 8,453).
*Pollen parent.*—Unnamed seedling.
Classification:
*Commercial.*—Miniature.

FLOWER

Observations made from specimens 18 weeks old at the beginning of observation and grown in a greenhouse environment at Somis, Calif. from August, 1999 to October 2000.

Blooming habit: Continuous.
Bud:
*Size.*—About ⅝ inch long when the petals start to unfurl.
*Form.*—The bud form is long and pointed ovoid.
*Color.*—When sepals first divide, bud color is Yellow Group 12A. When half blown, the upper sides of the petals are Yellow Group 12A; and the lower sides of the petals are Yellow Group 12A.
*Sepals.*—Color: Green Group 138B. Surface texture: Upper surface: Hairy. Lower surface: Glandular. Length: ⅝ to 1 inch. Width: ¼–⅜ inch. There are three normally to heavily appendaged sepals. There are two unappendaged sepals with hairy edges.
*Receptacle.*—Color: Green Group 137C. Shape: Funnel. Size: Small, about ¼"×¼". Surface: Smooth.

*Peduncle.*—Length: Short, averaging about 1½ inches. Surface: Glandular. Color: Green Group 137D. Strength: Stiff and erect.

Bloom:

*Size.*—Small. Average open size is 1¾ inches.

*Borne.*—Singly.

*Stems.*—Strength: Strong. Average length is about six inches.

*Form.*—When first open: High centered. Permanence: Flattens.

*Petalage.*—Number of petals under normal conditions: 25–30.

*Color.*—The upper sides of the petals are Yellow Group 12A. The reverse sides of the petals are Yellow Group 12A. The base of each petal has no color spot visible. The major color on the upper side is Yellow Group 12A.

*Variegations.*—None.

*Discoloration.*—The general tonality at the end of the first day: No change. No change through day sixteen when the petals will begin to dry.

*Fragrance.*—None.

Petals:

*Texture.*—Thick and leathery.

*Shape.*—Deltoid.

*Margin.*—Entire.

*Form.*—Tips slightly recurved, edges slighlty quilled.

*Arrangement.*—Imbricated. Petaloids in the center are few (1/16" to ¼" wide and ¼" to ½" long), with same color as petals.

*Persistence.*—Petals hang on and dry.

*Lastingness.*—On the plant: Very long (about 15–18 days). As a cut flower: Very long (about 18 days).

Reproductive parts:

*Anthers.*—Size: Length: 1 mm. Quantity: 45–50. Color: Yellow-Orange Group 16D. Arrangement: Regular around styles.

*Filaments.*—Color: Yellow Group 13C. Length: 2–3 mm.

*Pollen.*—Color: Yellow-Orange Group 21C.

*Styles.*—Color: Red Group 53B. Length: 2–3 mm.

*Stigmas.*—Color: Greyed-Orange Group 165D. Length: 1 mm.

*Pistils.*—Length: 3–4 mm. Number: 25–30.

*Hips.*—None formed.

Plant:

*Form.*—Bush.

*Growth.*—Vigorous, dwarf, upright and branching. At maturity grown outside, height is 24", width is 12". As a pot rose in a 5" pot, height is 10"–12", width is 8"–10".

Foliage: Number of leaflets on normal mid-stem leaves: 5 or 7.

*Size.*—Small, (3" long×2" wide).

*Quantity.*—Abundant.

*Color.*—New foliage: Upper surface: Yellow-Green Group 146C. Lower surface: Yellow-Green Group 146D. Old foliage: Upper surface: Green Group 137A. Lower surface: Green Group 137C.

Leaflets:

*Shape.*—Pointed oval.

*Texture.*—Leathery.

*Edge.*—Serrated.

*Serration.*—Single, small.

*Petiole rachis.*—Color: Yellow-Green Group 146B.

*Petiole underside.*—Rough with prickles and glands.

*Stipules.*—Short (about ¼ inch), serrated and bearded.

*Disease resistance.*—Susceptile to mildew and blackspot, resistant to rust under garden growing conditions.

Wood:

*New wood.*—Color: Yellow-Green Group 146C. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Short (2–3 mm), hooked slightly downward.

*Color when young.*—Greyed-Yellow Group 160D,

*Color when mature.*—Greyed-Brown Group 199D.

Small prickles:

*Quantity.*—On main stalks: None. On laterals: None.

Hardiness: Winter Hardy to Zone 5.

I claim:

1. A new and distinct variety of rose plant of the miniature class, substantially as herein shown and described, characterized particularly by its deep yellow flower color; long shelf life; ease of propagation as an own-root cutting; and an ability to force well throughout the year.

* * * * *

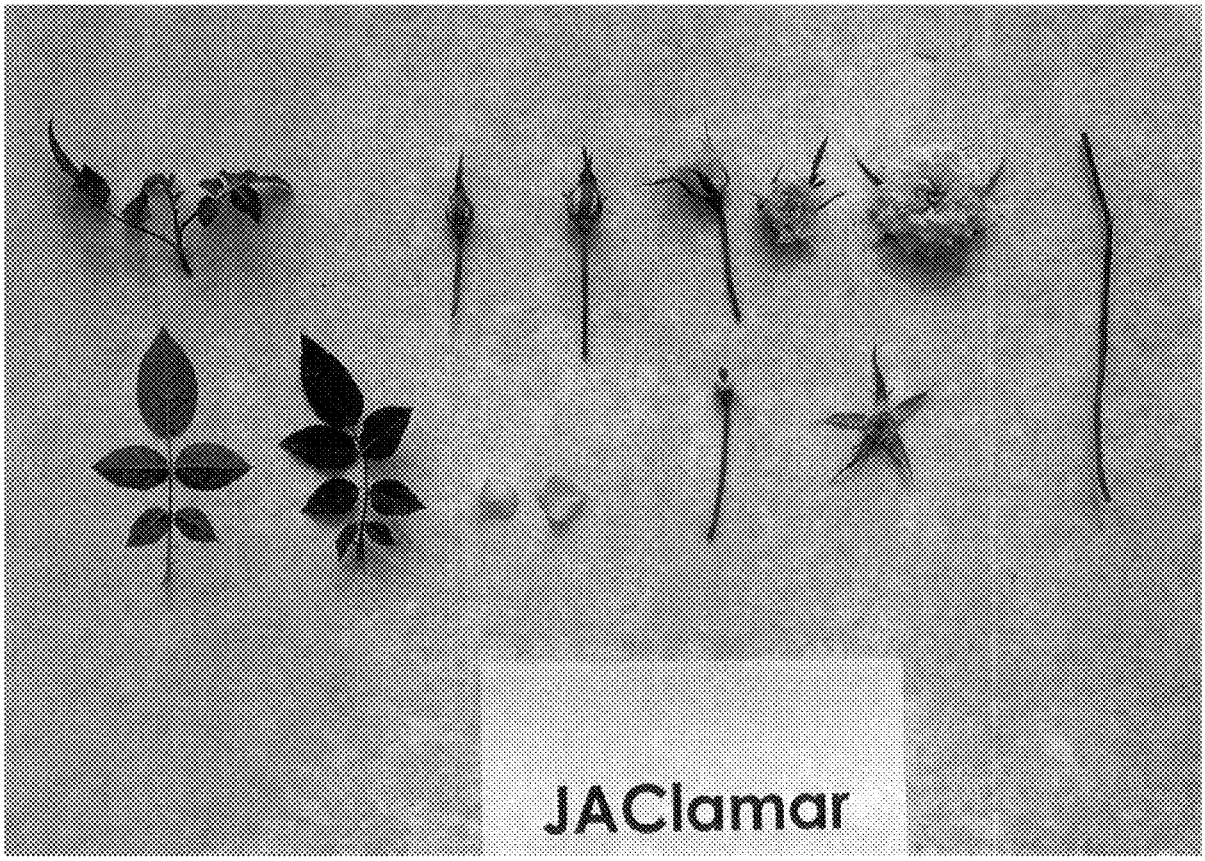
JAClamar

UNITED STATES PATENT AND TRADEMARK OFFICE

CERTIFICATE OF CORRECTION

PATENT NO. : PP 13,172 P2
DATED : November 5, 2002
INVENTOR(S) : Keith W. Zary

It is certified that error appears in the above-identified patent and that said Letters Patent is hereby corrected as shown below:

Column 1,
Line 16, “having a” should be -- having the --

Column 2,
Line 14, “MORply” should be -- MORpoly --

Column 4,
Line 23, “susceptile” should be -- susceptible --
Line 34, “160D,” should be -- 160D. --

Signed and Sealed this

Twenty-third Day of December, 2003

JAMES E. ROGAN
*Director of the United States Patent and Trademark Office*